United States Patent
Yamanashi et al.

(10) Patent No.: US 10,660,425 B2
(45) Date of Patent: May 26, 2020

(54) MAKEUP ASSISTANCE DEVICE, MAKEUP ASSISTANCE METHOD, AND MAKEUP ASSISTANCE PROGRAM

(71) Applicant: PANASONIC INTELLECTUAL PROPERTY MANAGEMENT CO., LTD., Osaka (JP)

(72) Inventors: Tomofumi Yamanashi, Kanagawa (JP); Rieko Asai, Osaka (JP); Aoi Muta, Osaka (JP); Chie Nishi, Kanagawa (JP); Kaori Ajiki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 373 days.

(21) Appl. No.: 14/770,167

(22) PCT Filed: Feb. 4, 2014

(86) PCT No.: PCT/JP2014/000583
§ 371 (c)(1),
(2) Date: Aug. 25, 2015

(87) PCT Pub. No.: WO2014/132566
PCT Pub. Date: Sep. 4, 2014

(65) Prior Publication Data
US 2016/0000209 A1 Jan. 7, 2016

(30) Foreign Application Priority Data

Feb. 28, 2013 (JP) ................................ 2013-039138

(51) Int. Cl.
*A45D 44/00* (2006.01)
*G06T 1/00* (2006.01)
(Continued)

(52) U.S. Cl.
CPC ........... *A45D 44/005* (2013.01); *A45D 44/00* (2013.01); *A61B 5/02055* (2013.01);
(Continued)

(58) Field of Classification Search
CPC .. A45D 44/005; A45D 44/00; G06K 9/00255; G06T 1/0007; G06T 11/00; A61B 5/02055
See application file for complete search history.

(56) References Cited

U.S. PATENT DOCUMENTS

2001/0037191 A1* 11/2001 Furuta .................. G06Q 10/087
703/6
2006/0132506 A1* 6/2006 Utsugi ..................... A61K 8/02
345/646

(Continued)

FOREIGN PATENT DOCUMENTS

EP 1975870 10/2008
JP 2001-104050 4/2001
(Continued)

OTHER PUBLICATIONS

Efros, Alexei, Image Compositing and Blending, 2007, http://graphics.cs.cmu.edu/courses/15-463/2007_fall/Lectures/blending.pdf, slide 7 (Year: 2007).*

(Continued)

*Primary Examiner* — James B Hull
*Assistant Examiner* — Lily M Del Valle
(74) *Attorney, Agent, or Firm* — Greenblum & Bernstein, P.L.C.

(57) ABSTRACT

Provided is a makeup assistance device that can assist in makeup/skin treatment more appropriately. This makeup assistance device comprises: a physical condition acquisition unit (260) that acquires physical condition information related to the physical condition of a person performing (Continued)

makeup and/or skin treatment; a makeup/skincare selection unit (280) that selects a makeup, which is how to apply makeup, and/or a skincare, which is how to treat the skin, on the basis of the acquired physical condition information; and a makeup/skincare presentation unit (290) that presents the selected makeup and/or skincare to the user performing makeup/skin treatment.

7 Claims, 13 Drawing Sheets

(51) Int. Cl.
- *G06K 9/00* (2006.01)
- *G06T 11/00* (2006.01)
- *A61B 5/0205* (2006.01)
- *A61B 5/021* (2006.01)
- *A61B 5/11* (2006.01)
- *A61B 5/00* (2006.01)

(52) U.S. Cl.
CPC ........ *G06K 9/00255* (2013.01); *G06T 1/0007* (2013.01); *G06T 11/00* (2013.01); *A45D 2044/007* (2013.01); *A61B 5/021* (2013.01); *A61B 5/1118* (2013.01); *A61B 5/4318* (2013.01); *A61B 5/441* (2013.01); *A61B 5/4806* (2013.01)

(56) References Cited

U.S. PATENT DOCUMENTS

| | | | |
|---|---|---|---|
| 2009/0245603 A1* | 10/2009 | Koruga | A45D 44/00 382/128 |
| 2010/0026717 A1* | 2/2010 | Sato | A45D 44/005 345/642 |
| 2010/0068247 A1* | 3/2010 | Mou | A45D 44/002 424/443 |
| 2010/0226531 A1 | 9/2010 | Goto | |
| 2012/0027269 A1* | 2/2012 | Fidaleo | G06Q 30/0268 382/118 |
| 2012/0223956 A1* | 9/2012 | Saito | A45D 44/005 345/582 |
| 2013/0271485 A1* | 10/2013 | Aoki | A45D 44/005 345/593 |
| 2015/0049111 A1 | 2/2015 | Yamanashi et al. | |
| 2015/0050624 A1 | 2/2015 | Yamanashi et al. | |
| 2015/0086945 A1 | 3/2015 | Yamanashi et al. | |
| 2015/0118655 A1 | 4/2015 | Yamanashi et al. | |
| 2015/0248581 A1 | 9/2015 | Gouda et al. | |
| 2015/0254500 A1 | 9/2015 | Izumi et al. | |
| 2015/0254501 A1 | 9/2015 | Yamanashi et al. | |
| 2015/0262403 A1 | 9/2015 | Yamanashi | |
| 2015/0366328 A1* | 12/2015 | Tamura | A45D 44/00 434/100 |
| 2016/0015152 A1 | 1/2016 | Ajiki et al. | |
| 2016/0022014 A1 | 1/2016 | Ajiki et al. | |

FOREIGN PATENT DOCUMENTS

| | | | |
|---|---|---|---|
| JP | 2001104050 A | * | 4/2001 |
| JP | 2001-346627 | | 12/2001 |
| JP | 2003-44837 | | 2/2003 |
| JP | 2003044837 A | * | 2/2003 |
| JP | 2006133856 A | * | 5/2006 |
| JP | 2007-175384 | | 7/2007 |
| JP | 2010-073008 | | 4/2010 |
| JP | 2010-086036 | | 4/2010 |
| JP | 2010-199756 | | 9/2010 |
| JP | 2012-181688 | | 9/2012 |

OTHER PUBLICATIONS

Extended European Search Report in European Patent Application No. 14757240.8, dated Feb. 16, 2016.
International Search Report in International Patent Application No. PCT/JP2014/000583, dated Mar. 11, 2014.

* cited by examiner

410

| SLEEPING HOURS | BODY TEMPERATURE | PHYSICAL CONDITION LEVEL |
|---|---|---|
| SHORTER THAN 4.5h | 37.5°C OR ABOVE | 1 |
| | BELOW 37.5°C | 1 |
| 4.5h OR LONGER AND SHORTER THAN 7h | 37.5°C OR ABOVE | 1 |
| | BELOW 37.5°C | 2 |
| 7h OR LONGER | 37.5°C OR ABOVE | 2 |
| | BELOW 37.5°C | 3 |

| FACIAL FEATURE VALUE GROUP | PHYSICAL CONDITION LEVEL | MAKEUP/SKIN CARE ID |
|---|---|---|
| FG 1 | 1 | F M 1 |
| FG 1 | 2 | F M 2 |
| FG 1 | 3 | F M 3 |
| FG 2 | 1 | F M 4 |
| FG 2 | 2 | F M 5 |
| FG 2 | 3 | F M 6 |
| ⋮ | ⋮ | ⋮ |

| MAKEUP/SKIN CARE ID | TYPE OF MAKEUP/SKIN CARE | COLOR | CONCENTRATION | RANGE | APPLICATION AMOUNT | COSMETICS ID |
|---|---|---|---|---|---|---|
| FM1 | T1 | C1 | D1 | A1 | — | I1 |
| FM1 | T2 | C2 | D2 | A2 | — | I2 |
| FM1 | T3 | C3 | D3 | A3 | — | I3 |
| FM1 | T4 | — | — | — | Q1 | I4 |
| ⋮ | ⋮ | ⋮ | ⋮ | ⋮ | ⋮ | ⋮ |

*FIG. 5*

| COSMETICS ID | COMPANY ID | ITEM NUMBER |
|---|---|---|
| I1 | B1 | b11 |
| I2 | B1 | b23 |
| ⋮ | ⋮ | ⋮ |

FIG. 6

| FACIAL PART ID | AREA | PERSON ID |
|---|---|---|
| P1 | R1 | H1 |
| P2 | R2 | H1 |
| ⋮ | ⋮ | ⋮ |

FIG. 10

MAKEUP ASSISTANCE DEVICE, MAKEUP ASSISTANCE METHOD, AND MAKEUP ASSISTANCE PROGRAM

TECHNICAL FIELD

The present invention relates to a makeup assisting apparatus, a makeup assisting method and a makeup assisting program for assisting facial makeup (cosmetic makeup).

BACKGROUND ART

In recent years, the way of making up the face (hereinafter, simply referred to as "makeup") and the way of maintaining the skin (hereinafter referred to as "skin care") have been diversified. Therefore, it has become difficult, particularly for a person who has no sufficient knowledge about makeup to select appropriate makeup and skin maintenance from an infinite number of options because it takes an enormous amount of time and effort to actually try, judge and compare various types of makeup and skin care.

Under such circumstances, PTL 1 and PTL 2 disclose techniques in which makeup that matches the feature of the face is selected, and a simulation image of the face on which the selected makeup is applied is created and presented, for example. In the techniques disclosed in PTL 1 and PTL 2, a captured image of a face that is subjected to makeup is acquired, the feature of the face is extracted, and makeup that matches the feature of the face is selected based on a selection criteria set in advance. Then, in the techniques disclosed in PTL 1 and PTL 2, on the acquired image, an image indicating a state of makeup obtained by applying the selected makeup on the face is superimposed to create and display a simulation image.

In addition, PTL 3 discloses a technique in which skin care that matches the condition of the skin and the schedule is selected and presented, for example. In the technique disclosed in PTL 3, skin care information is generated based on the present condition of the skin and the schedule of the user, and the generated skin care information is presented.

With the above-mentioned conventional techniques, it is possible to more quickly and easily select and perform makeup that matches the feature of the face, or skin care reflecting the present condition of the skin and the schedule.

CITATION LIST

Patent Literature

PTL 1
Japanese Patent Application Laid-Open No. 2001-346627
PTL 2
Japanese Patent Application Laid-Open No. 2007-175384
PTL 3
Japanese Patent Application Laid-Open No. 2010-199756
PTL 4
Japanese Patent Application Laid-Open No. 2003-44837

Non-PTL

Non-PTL 1
Tomio SUDA, and other seven authors, "Questionnaire about fatigue and skin", [online], April 2012, Ornithine laboratory, [searched on Feb. 27, 2013], the Internet <URL: http://ornithine.jp/information/2012/04/post-9.html>

SUMMARY OF INVENTION

Technical Problem

However, with the conventional techniques, inadequate makeup/skin care may be selected since the condition of the face changes with time. For example, when makeup which does not include application of concealer for concealing dark circles below the eyes is selected because dark circles were not found at the time of makeup in the morning, deep dark circles may appear below the eyes in the evening because of fatigue. Accordingly, the conventional technology may not appropriately achieve assistance of makeup/skin maintenance.

An object of the present invention is to provide a makeup assisting apparatus, a makeup assisting method, and a makeup assisting program which can appropriately assist makeup/skin maintenance.

Solution to Problem

A makeup assisting apparatus of embodiments of the present invention includes: a physical condition acquiring section that acquires physical condition information relating to a physical condition of a person who is subjected to makeup and/or skin maintenance; a makeup/skin care selecting section that selects make-up and/or skin care based on the acquired physical condition information, the make-up being a way of performing the makeup, the skin care being a way of performing the skin maintenance; and a makeup/skin care presenting section that presents the selected makeup and/or the selected skin care to a user who performs the makeup and/or the skin maintenance.

A makeup assisting method of embodiments of the present invention includes: acquiring physical condition information relating to a physical condition of a person who is subjected to makeup and/or skin maintenance; selecting make-up and/or skin care based on the acquired physical condition information, the make-up being a way of performing the makeup, the skin care being a way of performing the skin maintenance; and presenting the selected makeup and/or the selected skin care to a user who performs the makeup and/or the skin maintenance.

A makeup assisting program of embodiments of the present invention causes a computer to execute processing including: acquiring physical condition information relating to a physical condition of a person who is subjected to makeup and/or skin maintenance; selecting make-up and/or skin care based on the acquired physical condition information, the make-up being a way of performing the makeup, the skin care being a way of performing the skin maintenance; and presenting the selected makeup and/or the selected skin care to a user who performs the makeup and/or the skin maintenance.

Advantageous Effects of Invention

According to the present invention, assistance of makeup/skin maintenance can be appropriately performed.

BRIEF DESCRIPTION OF DRAWINGS

FIG. 3 shows an exemplary physical condition table of Embodiment 2;

FIG. 4 shows an exemplary makeup/skin care table of Embodiment 2;

FIG. 5 shows an exemplary makeup/skin care information table of Embodiment 2;

FIG. 6 shows an exemplary cosmetics information table of Embodiment 2;

FIG. 10 shows exemplary facial part information of Embodiment 2;

DESCRIPTION OF EMBODIMENTS

In the following, embodiments of the present invention will be described in detail with reference to the accompanying drawings.

Embodiment 1

Embodiment 1 of the present invention is an example of a basic mode of the present invention.

Figure 1:
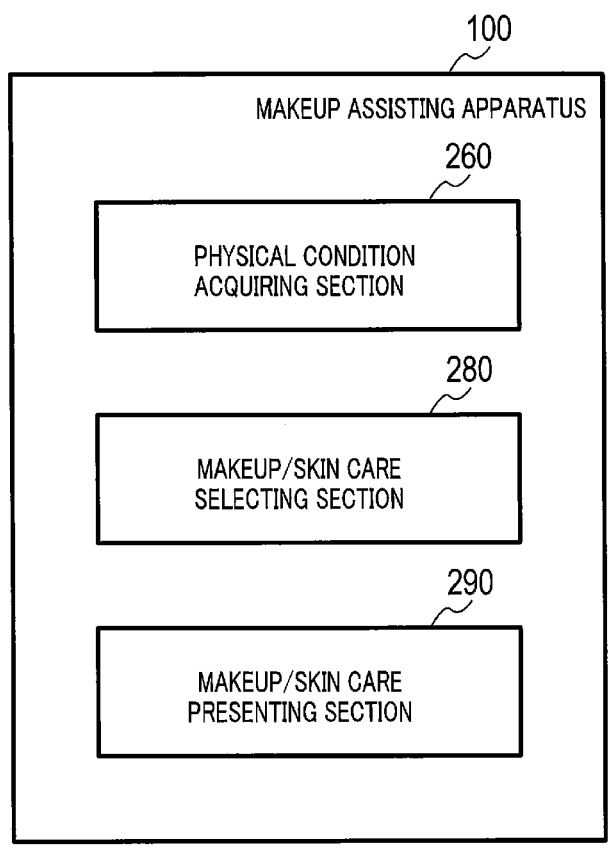
FIG. 1 is a block diagram illustrating an exemplary configuration of a makeup assisting apparatus according to Embodiment 1 of the present invention.

FIG. 1 is a block diagram illustrating an exemplary configuration of a makeup assisting apparatus according to the present embodiment.

In FIG. 1, makeup assisting apparatus 100 includes physical condition acquiring section 260, makeup/skin care selecting section 280, and makeup/skin care presenting section 290.

Physical condition acquiring section 260 acquires physical condition information relating to the physical condition of a person subjected to makeup/skin maintenance (hereinafter referred to as "person subjected to makeup").

Makeup/skin care selecting section 280 selects skin care that is a way of makeup/skin maintenance based on the acquired physical condition information.

Makeup/skin care presenting section 290 presents the selected makeup/skin care to a user (for example, the person subjected to makeup him/herself) who performs makeup/skin maintenance for the person subjected to makeup.

Makeup assisting apparatus 100 has, for example, a central processing unit (CPU), a storage medium such as a read-only memory (ROM) having a control program stored therein, and a working memory such as a random access memory (RAM), although these components are not illustrated. In this case, the above-described functions of the sections are implemented by the CPU executing the control program.

Makeup assisting apparatus 100 can present to the user the makeup/skin care selected in consideration of the physical condition of the person subjected to makeup. The degree of variation of the facial condition is greatly influenced by the physical condition of the person in particular (see, for example, Non-PTL 1). Therefore, by selecting makeup/skin care in consideration of the physical condition of the person subjected to makeup, makeup/skin care more suitable for the facial condition after a certain time has passed can be presented. That is, makeup assisting apparatus 100 can select makeup/skin care in consideration of the facial condition after a certain time has passed, and can more appropriately achieve assistance of makeup/skin maintenance.

Embodiment 2

Embodiment 2 of the present invention is an example of a specific mode of the present invention. Embodiment 2 is an exemplary case where the present invention is applied in an apparatus having a display provided with a touch panel and a digital camera.

<Explanation of Terms>

First, the terms used in the present embodiment are explained.

"Physical condition information" refers to information about the physical condition of a person, which relates to at least one of the sleeping hours, body temperature, amount of physical activity, opening degree of an eyelid, frequency of eyeblink, stage in the menstrual cycle, blood pressure, and skin condition.

A "facial part" refers to a part characterizing impression of the face, such as eyes, eyebrows, nose, cheekbones, lips and an outline.

"Facial part ID" refers to identification information of the facial part.

An "area of the facial part" refers to an area occupied by the facial part on an image or in real space, and includes a position of a feature point of the facial part, such as corners of the eyes.

A "facial feature value" refers to a value of a predetermined parameter which indicates features of the face. Here, the facial feature value is multivariate data including a plurality of values such as a ratio of a length of the face with respect to a width of the face, a ratio of a length of the nose with respect to a distance between both eyes and a ratio of a width of the eye with respect to the width of the face.

"Makeup" indicates the way (type) of applying makeup such as eye shadows and lipsticks that corrects impression of features of the facial part to improve aesthetics, and includes at least a color, application concentration and application range of a skin cosmetic agent.

"Skin care" refers to the way (kind) of action taken for the purpose of adjusting the condition of the skin (skin maintenance). Such action includes, for example, care applied to the skin to improve the skin condition and action for improving the skin condition internally (or for improving inner beauty). The former includes, for example, application of basic skin care such as lotion and serum, facial massage and the like. The latter includes, for example, intake of supplements, intake of organic food, exercises such as yoga, adjustment of indoor environment and the like. The way of applying basic skin care includes the type of basic skin care, the application amount of each time, an application range, an application frequency, hours at which basic skin care is applied, the way of application, and the like.

"Makeup/skin care information" refers to information representing the detail of makeup/skin care.

"Cosmetics information" refers to information relating to cosmetics for applying the makeup/skin care.

"Type of makeup/skin care" refers to the type of makeup such as "foundation," "eye shadow," "lipstick," and "blush"

that are identified by at least by the positional relationship with facial parts, and the type of skin care such as "lotion" and "serum."

"Makeup/skin care ID" refers to identification information of makeup/skin care.

"Cosmetics ID" refers to identification information of cosmetics for the skin, which can specify cosmetics information.

"Change in Facial Condition" includes change in the degree of at least one of drying of the skin, secretion of sebum, secretion of sweat, dark circle, wrinkles, slack of the skin, relaxation of the muscle, excitation of the muscle, poorness of complexion, and skin roughening.

"Physical condition level" refers to a value indicating the quality level of the physical condition.

<Configuration of Makeup Assisting Apparatus>

Next, a configuration of the makeup assisting apparatus according to the present embodiment is described.

Figure 2:
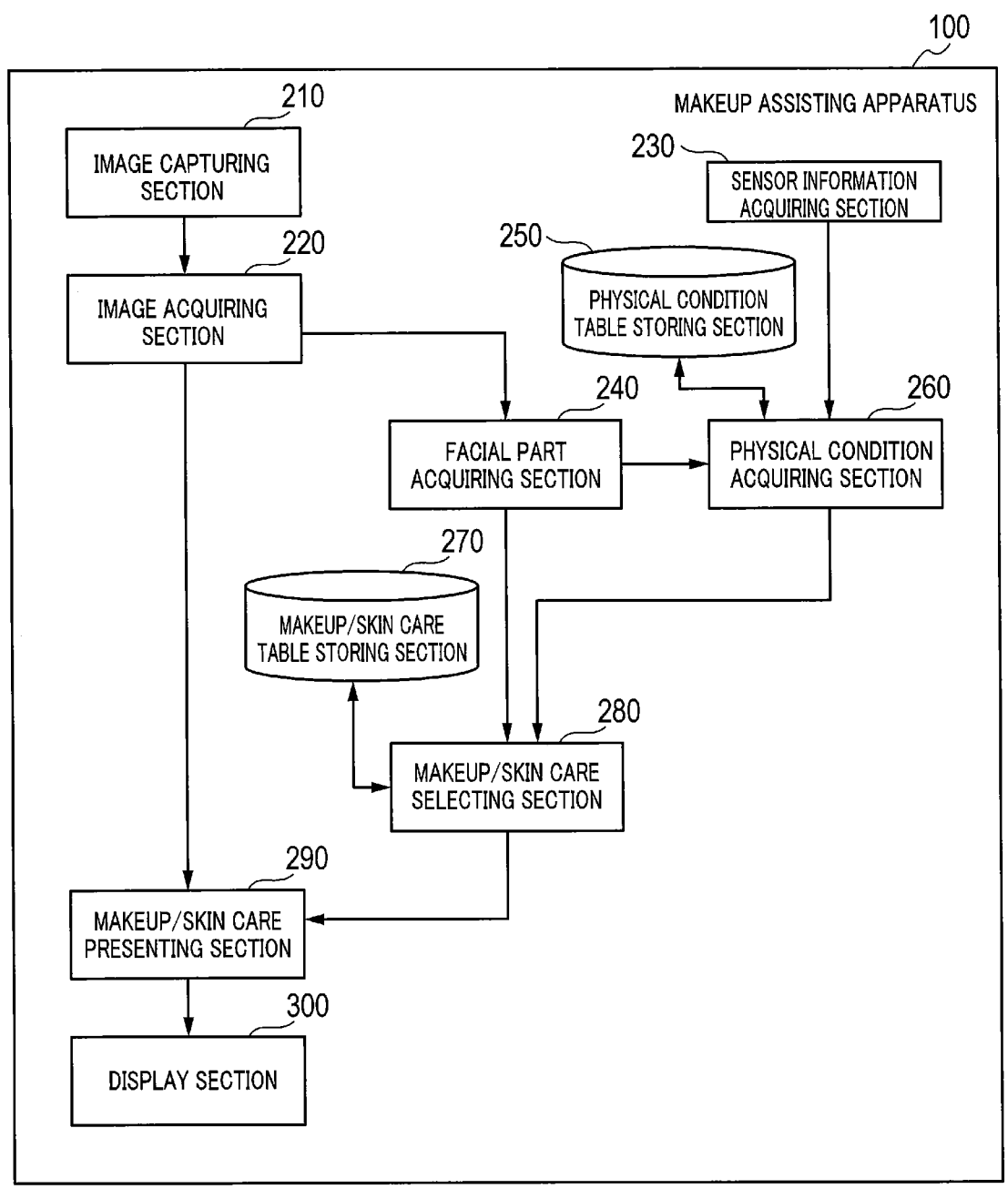
FIG. 2 is a block diagram illustrating an exemplary configuration of a makeup assisting apparatus according to Embodiment 2 of the present invention.

FIG. 2 is a block diagram illustrating an exemplary configuration of the makeup assisting apparatus according to the present embodiment.

In FIG. 2, makeup assisting apparatus 100 includes image capturing section 210, image acquiring section 220, sensor information acquiring section 230, facial part acquiring section 240, physical condition table storing section 250, physical condition acquiring section 260, makeup/skin care table storing section 270, makeup/skin care selecting section 280, makeup/skin care presenting section 290, and display section 300.

Image capturing section 210 is, for example, a digital video camcorder, and captures a moving image of the face of a person subjected to makeup. Capturing section 210 outputs the captured moving image to image acquiring section 220. The moving image includes a plurality of time-series images (frame images). It is to be noted that, in the present embodiment, the person subjected to makeup is the user of makeup assisting apparatus 100.

Image acquiring section 220 sequentially acquires the images included in the moving image from the received moving image. Image acquiring section 220 outputs the acquired image to facial part acquiring section 240 and makeup/skin care presenting section 290.

Sensor information acquiring section 230 acquires sensor information required for acquiring the physical condition information of the user from various sensors (not illustrated). Then, sensor information acquiring section 230 outputs the acquired sensor information to physical condition acquiring section 260. The sensor information is acquired from, for example, an information inputting apparatus such as a sleep meter, a thermometer, a physical activity meter, a digital camera, and a touch panel.

In the present embodiment, through the radio communication with a sleep meter and a thermometer (not illustrated) used by the user, sensor information acquiring section 230 acquires from the meters sleeping hours and body temperature as sensor information.

Facial part acquiring section 240 acquires an area of the facial part of the face from each of the received images. The area of the facial part is acquired, for example, through matching between each partial area of the image and a template image of each facial part prepared in advance (for example, see PTL 4). Facial part acquiring section 240 outputs information indicating identification information and the area of the acquired facial part (hereinafter, referred to as "facial part information") to makeup/skin care selecting section 280.

Physical condition table storing section 250 stores a physical condition table. The physical condition table is a table describing the corresponding relation among contents of sensor information and a plurality of physical condition levels.

FIG. 3 illustrates an exemplary physical condition table.

As illustrated in FIG. 3, in physical condition table 410, physical condition level 413 is described for each combination pattern of sleeping hours 411 and body temperature 412. For example, physical condition level 413 of "1" is associated with the combination of sleeping hours 411 of "shorter than 4.5 h" and body temperature 412 of "37.5° C. or above." This means that the case where the sleeping hours is shorter than 4.5 h and the body temperature is 37.5° C. or above corresponds to the physical condition level of "1." It is to be noted that, in the present embodiment, the physical condition level indicates that the greater the value, the physical condition is more favorable.

In makeup/skin care table storing section 270 of FIG. 2, a makeup/skin care table is stored. The makeup/skin care table is a table that describes, in association with the contents of the physical condition information, the makeup and/or the skin care suitable for change in a facial condition of the person that is estimated when a physical condition of the person matches any of the contents of the physical condition information. It is to be noted that, in the present embodiment, the contents of the physical condition information are a plurality of physical condition levels. In addition, in the makeup/skin care table of the present embodiment, the facial feature value to be acquired from a facial part and makeup appropriate for the face having the facial feature value are associated with one another.

It is assumed in the present embodiment that principal component analysis is performed in advance on samples of the facial feature value of an unspecified number of faces to which makeup experts have applied makeup in the past. It is assumed that the results of the principal component analysis are grouped in advance using a publicly known principal component grouping method in which it is determined based on a determination criterion such as whether or not a principal component value is 1 σ or higher. Further, it is assumed that in the makeup/skin care table, makeup which has been applied in the past to the face belonging to the group is registered for each facial feature value group.

FIG. 4 illustrates an exemplary makeup/skin care table.

As illustrated in FIG. 4, in makeup/skin care table 420, makeup/skin care ID 423 is described for each combination of facial feature value group 421 and physical condition level 422. For example, makeup/skin care ID 423 of "FM1" is associated with the combination of facial feature value group 421 of "FG1" and physical condition level 422 of "1." This indicates that when the facial feature value of the user is FG1 and the physical condition level of the user is 1, the makeup/skin care represented by makeup/skin care ID of "FM1" is appropriate.

For example, in addition, in comparison with the makeup represented by makeup/skin care ID 423 of "FM3," the makeup represented by makeup/skin care ID 423 of "FM1," which corresponds to a physical condition level lower than that of the makeup represented by makeup/skin care ID 423 of "FM3," requests a greater application amount of concealer for concealing dark circle. In comparison with the skin care represented by makeup/skin care ID 423 of "FM3," the skin care represented by makeup/skin care ID 423 of "FM1," which corresponds to a physical condition level lower than that of the skin care represented by makeup/skin care ID 423 of "FM3," requests a greater application amount of lotion.

It is to be noted that the trends of makeup/skin care change frequently, and therefore the makeup/skin cares to be presented should be changed frequently. For this reason, it is desirable to periodically update makeup/skin care table 420 from a server on the Internet through a communication circuit (which is not illustrated) provided at makeup assisting apparatus 100, for example.

In addition, makeup/skin care table storing section 270 of FIG. 2 stores a makeup/skin care information table and a cosmetics information table. The makeup/skin care information table is a table describing the makeup/skin care information of the makeup/skin cares represented by makeup/skin care ID 423 described in makeup/skin care table 420 (see FIG. 4). The cosmetics information table is a table describing the cosmetics information of the makeup/skin care represented by the makeup/skin care information described in the makeup/skin care information table.

FIG. 5 illustrates an exemplary makeup/skin care information table stored in makeup/skin care table storing section 270. Here, an exemplary case where skin care is the way of applying basic skin care is described.

As illustrated in FIG. 5, in makeup/skin care information table 430, makeup/skin care ID 431, type of makeup/skin care 432, color 433, concentration 434, range 435, application amount 436 and cosmetics ID 437 are associated with one another.

Makeup/skin care ID 423 (see FIG. 4) of makeup/skin care table 420 is associated with makeup/skin care ID 431. Type of makeup/skin care 432, which is illustrated in a simplified manner, specifically includes "foundation," "eye shadow," "lipstick," "blush," and "lotion." Color 433, which is illustrated in a simplified manner, specifically includes an RGB value, a gloss level, and the like. Concentration 434, which is illustrated in a simplified manner, specifically includes a level of permeability, the way of gradation, and the like when an image is superimposed on the image of the face. Range 435, which is illustrated in a simplified manner, specifically includes a relative coordinate group from a feature point, a set of a relative position of a central point with respect to a feature point and a radius, and the like.

A set of color 433, concentration 434, and range 435 includes at least information required for forming an image. That is, in the present embodiment, the makeup/skin care information about makeup includes at least information required for forming, from a facial image, an image of the face on which makeup has been performed.

In addition, application amount 436 represents the application amount of basic skin care. Application amount 436, which is illustrated in a simplified manner, is text information such as "normal amount" and "relatively large."

FIG. 6 illustrates an exemplary cosmetics information table stored in makeup/skin care table storing section 270.

As illustrated in FIG. 6, in cosmetics information table 440, cosmetics ID 441, company ID 442, and item number 443 are associated with one another.

Cosmetics ID 441 corresponds to cosmetics ID 437 (see FIG. 5) of makeup/skin care information table 430. Company ID 442 is a name or an identifier of the company which manufactures or sells the skin cosmetics. Item number 443 is an item number of the skin cosmetics.

It is to be noted that makeup/skin care table 420, makeup/skin care information table 430, and cosmetics information table 440 illustrated in FIG. 4 to FIG. 6 may be integrated into one table.

Makeup/skin care selecting section 280 of FIG. 2 acquires the facial feature value. It is to be noted that makeup/skin care selecting section 280 may acquire the facial feature value from the facial part information received from facial part acquiring section 240 or from an image by analyzing the image acquired by image acquiring section 220. Makeup/skin care selecting section 280 selects makeup/skin care information for each facial part based on the acquired feature values of the facial part and the received physical condition level with reference to makeup/skin care table 420 (see FIG. 4) and makeup/skin care information table 430 (see FIG. 5). That is, makeup/skin care selecting section 280 selects makeup/skin care based on the acquired facial feature value and physical condition information. Then, makeup/skin care selecting section 280 outputs the selected makeup/skin care information to makeup/skin care presenting section 290.

It is to be noted that, as described above, in makeup/skin care table 420, makeup/skin care ID 423 is registered for each facial feature value group. Therefore, makeup/skin care selecting section 280 determines facial feature value group 421 of the facial feature value acquired from the face, which is registered in makeup/skin care table 420, and makeup/skin care selecting section 280 selects makeup/skin care ID 423 corresponding to the determined facial feature value group 421. This determination is made, for example, by calculating a distance between the acquired facial feature value and a representative value (centroid) of each group.

In addition, makeup/skin care selecting section 280 refers to cosmetics information table 440 (see FIG. 6) to acquire cosmetics information of the makeup selected for each facial part, and acquires cosmetics information of the skin care selected for each facial part. By makeup/skin care selecting section 280, the cosmetics information thus acquired is associated with makeup/skin care information, and is output to makeup/skin care presenting section 290.

Makeup/skin care presenting section 290 presents the selected makeup/skin care to the user performing makeup/skin maintenance. To be more specific, based on the received image and makeup/skin care information, makeup/skin care presenting section 290 forms an simulation image, and outputs the formed simulation image to display section 300. Here, a simulation image is obtained by superimposing on a received (captured) image an image of a face on which selected makeup has been applied.

It should be noted that the image is superimposed by, for example, a publicly-known image combining process such as an alpha ($\alpha$) blending process. In this case, an alpha value ($\alpha$) is set according to concentration of makeup. The alpha blending process is expressed with, for example, the following Equations 1 to 3:

$$R = r_2 \times \alpha + r_1 \times (1-\alpha) \quad (1)$$

$$G = g_2 \times \alpha + g_1 \times (1-\alpha) \quad (2)$$

$$B = b_2 \times \alpha + b_1 \times (1-\alpha) \quad (3)$$

where $r_1$, $g_1$ and $b_1$ are RGB values of an arbitrary area in the captured image, $r_2$, $g_2$ and $b_2$ are RGB values of the corresponding area in an image of makeup, and R, G and B are RGB values of the corresponding area in the simulation image.

Further, it is assumed that an order of application when makeup is applied to the face in an overlapped manner (hereinafter, referred to as an "application order") is set for each makeup, and an image in a case where the makeup is applied is presented as an image shaded with density according to the concentration. The application order defines, for example, blush should be applied after foundation is applied. In this case, the images may be superimposed on the captured image by overpainting the image of each makeup in an order according to the application order.

Further, makeup/skin care presenting section 290 forms simulation images sequentially using once selected facial and makeup for each of the images included in the moving image acquired from image acquiring section 220 and outputs the simulation images to display section 300 (makes display section 300 display the simulation images). That is, makeup/skin care presenting section 290 keeps and presents the makeup selected once for one moving image.

In addition, makeup/skin care presenting section 290 further presents the makeup/skin care information of the selected skin care and the cosmetics information of the selected makeup/skin care. To be more specific, makeup/skin care presenting section 290 superimposes or adds an image or text indicating the received cosmetics information and makeup/skin care information of skin care on or to the above-described simulation image.

Display section 300 which is, for example, a display portion of a display with touch panel, displays (presents) the received simulation image, makeup/skin care information of skin care and cosmetics information to the user of makeup assisting apparatus 100.

It should be noted that makeup assisting apparatus 100 includes, for example, a CPU, a storage medium such as a ROM having a control program stored therein, and a working memory such as a RAM, which are not illustrated. In this case, the above-described functions of the sections are implemented by the CPU executing the control program.

Makeup assisting apparatus 100 having the above-mentioned configuration can present to the user the makeup/skin care selected in consideration of the physical condition of the user. The degree of the change in facial condition is greatly influenced by the physical condition of the user (see, for example, non-PTL 1). Therefore, by selecting makeup/skin care in consideration of the physical condition of the user, it is possible to present makeup/skin care more suitable for the facial condition after a certain time has passed.

<Operation of Makeup Assisting Apparatus>

Next, operation of makeup assisting apparatus 100 is described.

Figure 7:
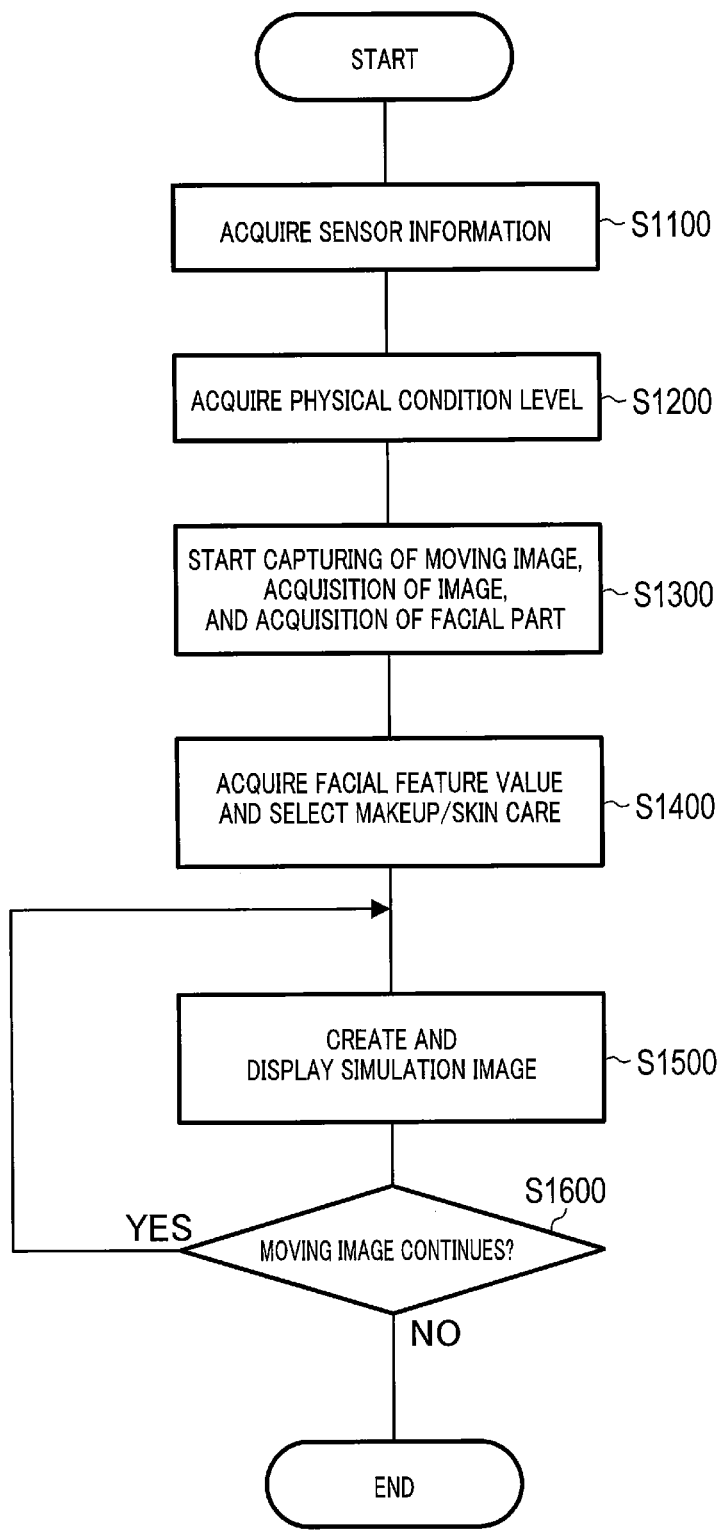
FIG. 7 is a flowchart of an exemplary operation of the makeup assisting apparatus according to Embodiment 2.

FIG. 7 is a flowchart of exemplary operation of makeup assisting apparatus 100.

First, at step S1100, sensor information acquiring section 230 acquires the sleeping hours and body temperature of the user as sensor information.

At step S1200, physical condition acquiring section 260 acquires the physical condition level of the user based on the acquired sensor information.

At step S1300, image capturing section 210 starts capturing of the moving image of the face of the user, and image acquiring section 220 starts acquisition of images of the captured moving image. In addition, the facial part acquiring section starts acquisition of a facial part included in the image.

Figure 8:
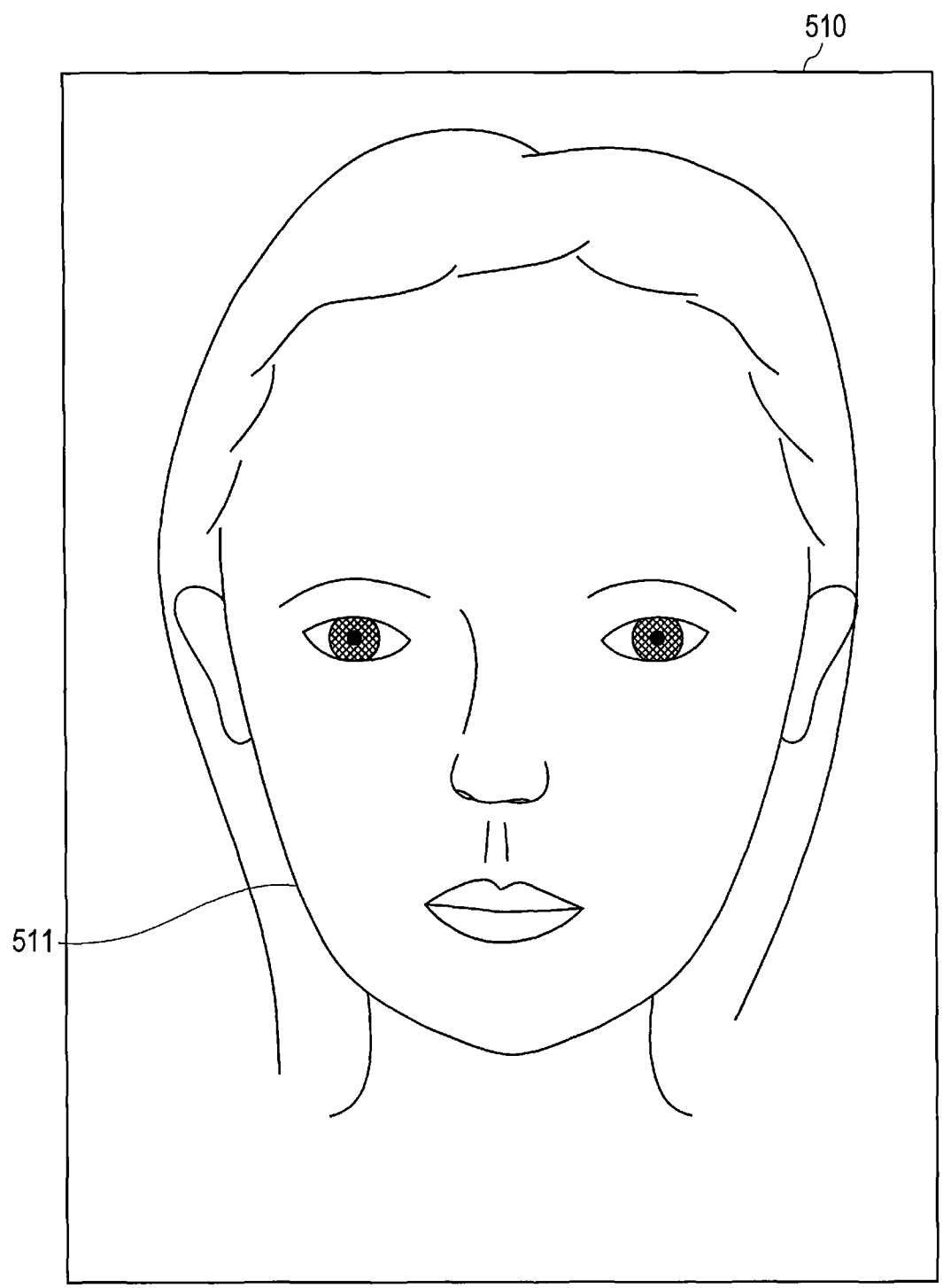
FIG. 8 illustrates an exemplary image of Embodiment 2.

At this time, facial part acquiring section 240 for example, extracts feature points (of the facial part) of the face from image 510 by analyzing image 510 (see FIG. 8). Facial part acquiring section 240 acquires an area formed with the feature points constituting the same facial part as an area of the facial part. Facial part acquiring section 240 generates facial part information from the acquired area of the facial part.

FIG. 8 illustrates an exemplary image acquired in step S1300 in FIG. 7.

As illustrated in FIG. 8, image 510 includes an image of the face of the user (hereinafter, referred to as a "face image") 511. Here, the user wears no makeup.

It is assumed that the user is in a good physical condition after eight hours of sleep, and has a body temperature of 36.5 degrees.

Figure 9:
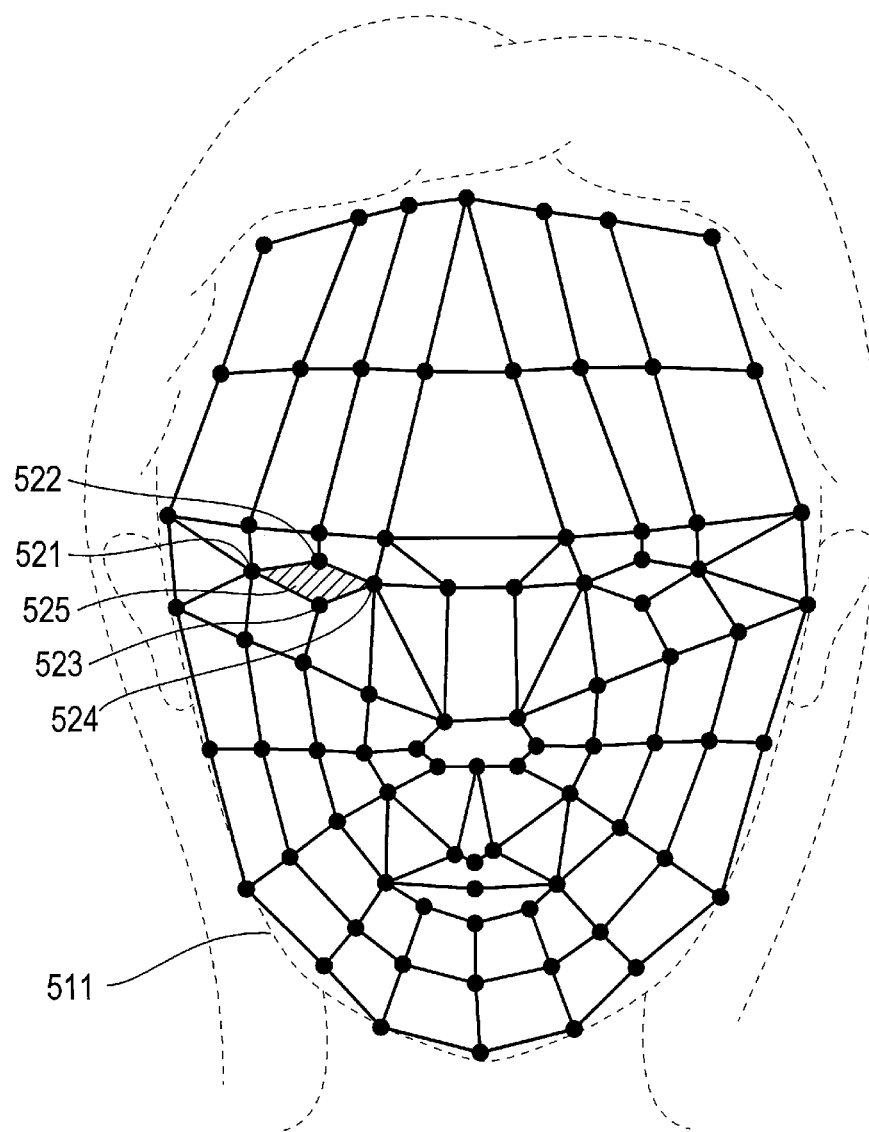
FIG. 9 illustrates exemplary positions of feature points of the face.

FIG. 9 illustrates exemplary positions of feature points of the face, extracted at step S1300 of FIG. 7.

As illustrated in FIG. 9, a plurality of feature points (expressed with symbols "●") are extracted from face image 511. For example, first to fourth feature points 521, 522, 523 and 524 constitute the right eye. Therefore, facial part acquiring section 240 acquires area 525 enclosed by first to fourth feature points 521 to 524 as an area of the right eye.

FIG. 10 illustrates an exemplary facial part information generated at step S1300 of FIG. 7.

As illustrated in FIG. 10, facial part information 530, for example, describes area 532 and person ID 533 for each facial part ID 531. Facial part ID 531 is identification information of the facial part such as the left eye and the upper lip. Area 532, which is information indicating a range of the area of the facial part in the image, is a list of coordinate values of a coordinate system set on the image, for example. Person ID 533 is identification information of the person. As person ID 533, for example, a value designated by the user through operation to a display with touch panel or the like is set every time capturing is started.

At step S1400 of FIG. 7, makeup/skin care selecting section 280 acquires the facial feature value. The facial feature value is, as described above, multivariate data regarding a predetermined parameter indicating the features of the face. Makeup/skin care selecting section 280 acquires the facial feature value from, for example, image 510 (see FIG. 8), a group of facial feature points (see FIG. 9), or the facial part information (see FIG. 10). Makeup/skin care selecting section 280 selects makeup/skin care based on the acquired facial feature value and physical condition level.

At step S1500, makeup/skin care presenting section 290 creates a simulation image based on the makeup/skin care information about makeup, and makes display section 300 display the simulation image. At this time, makeup/skin care presenting section 290 makes display section 300 display the makeup/skin care information about skin care and the cosmetics information of makeup/skin care.

Figure 11:
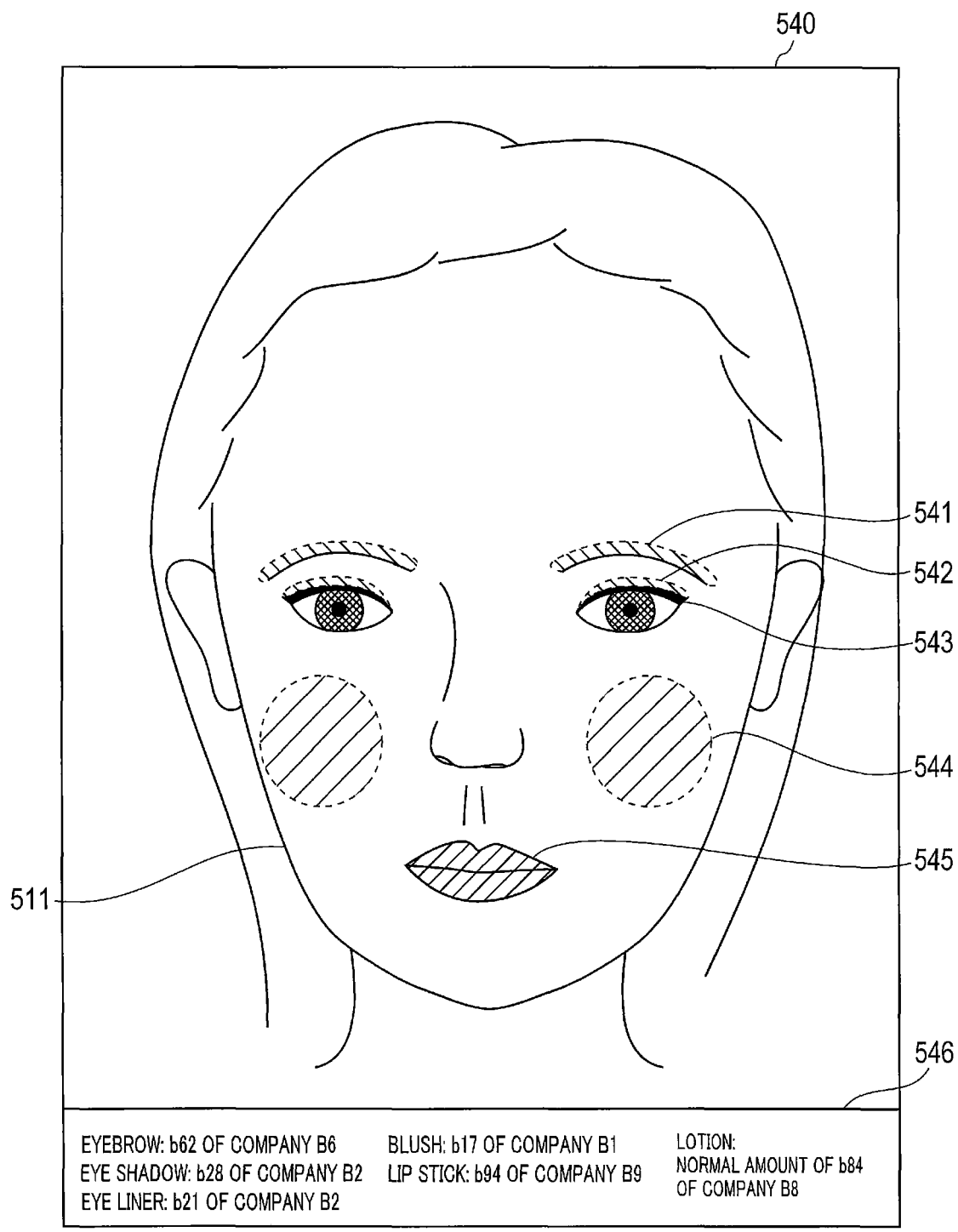
FIG. 11 illustrates an exemplary simulation image of Embodiment 2.

FIG. 11 illustrates an exemplary simulation image created at step S1500 of FIG. 7.

As illustrated in FIG. 11, simulation image 540 is an image in which images 541, 542, 543, 544 and 545 of makeup such as eyebrow, eye shadow, eye liner, blush and lip stick are superimposed on image 511.

In addition, simulation image 540 is additionally provided with information display area 546 where makeup/skin care information of skin care and cosmetics information of makeup/skin care are shown. That is, in simulation image 540, the cosmetics information of the skin cosmetics required for applying the selected makeup and details of skin care are also displayed.

It is to be noted that the text displayed in information display area 546 may be registered in advance in makeup/skin care information table 430 (see FIG. 5) or cosmetics information table 440 (see FIG. 6). Alternatively, the text displayed on information display area 546 may be generated by makeup/skin care presenting section 290 based on the makeup/skin care information and the cosmetics information.

If the user likes makeup shown in the displayed simulation image 540 or skin care presented in the displayed simulation image 540, the user can get required skin cosmetics based on the displayed cosmetics information and can easily put on her makeup actually.

At step S1600, image acquiring section 220 determines whether or not input of a moving image continues. If image acquiring section 220 determines that input of a moving image continues (S1600: Yes), the flow returns to step S1500 and shifts to process on the subsequent image. Meanwhile, if image acquiring section 220 determines that input of a moving image is finished (S1600: No), a series of process is finished.

The operation as described above makes it possible for makeup assisting apparatus 100 to present to the user makeup in association with the corresponding area while following the moving image. Therefore, the user can confirm the effect of makeup while changing the orientation or the expression of the face and can experience a sense as if she saw herself actually having put on the makeup in the mirror.

When the user is in good physical condition, the facial condition of the user is maintained in a good condition even after a certain time has elapsed as illustrated in FIG. 8. However, when the user is not in good physical condition, the facial condition tends to change, and may change with time from the condition at the time of the simulation of makeup.

Figure 12:
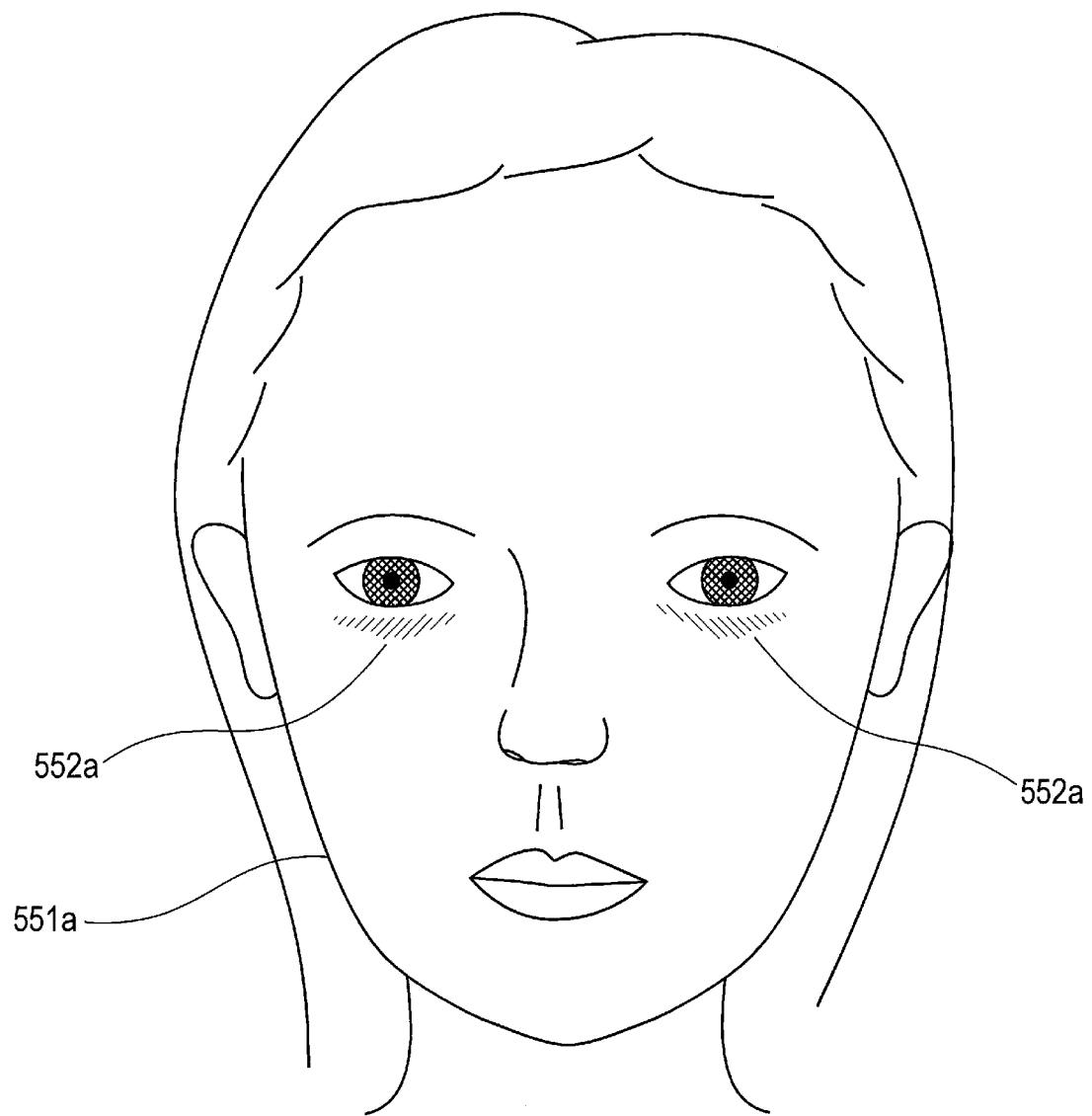
FIG. 12 illustrates an exemplary facial condition after a certain time has passed in Embodiment 2.

FIG. 12 illustrates an exemplary facial condition after a certain time has passed in the case where the physical condition of the user is not good. FIG. 12 illustrates an exemplary case of a user after only four hours of sleep.

As illustrated in FIG. 12, deep dark circle 552*a* appears below the eyes of face 551*a* of the user. Therefore, when the physical condition of the user is not good, it is desirable to preliminarily perform makeup that can conceal dark circle 552*a*.

In this case, as described above, makeup assisting apparatus 100 according to the present embodiment proposes makeup/skin care suitable for the change in face condition based on the physical condition on the basis of physical condition information.

Figure 13:
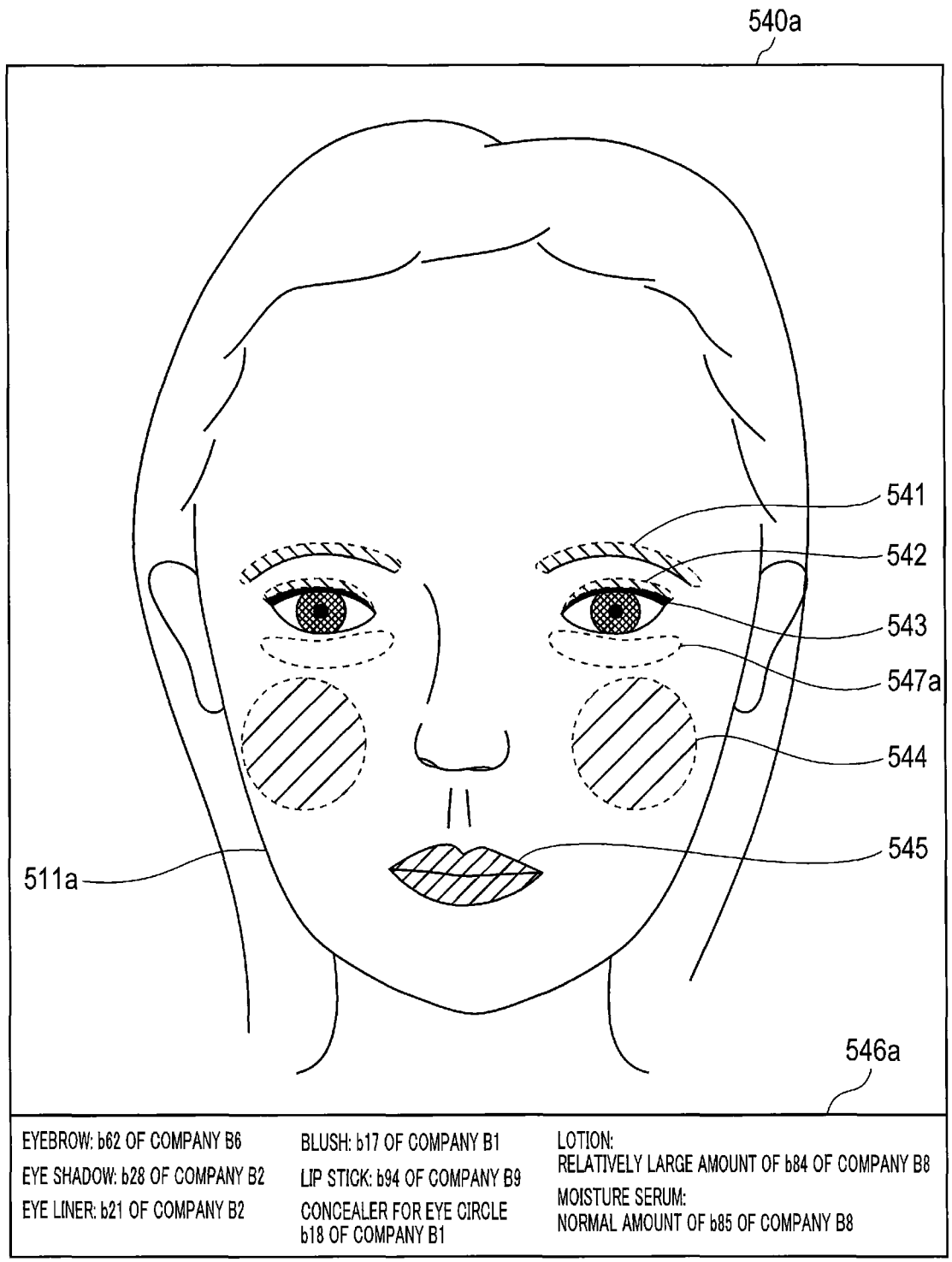
FIG. 13 illustrates another exemplary simulation image of Embodiment 2.

FIG. 13 illustrates an exemplary simulation image presented to a user after only four hours of sleep.

As illustrated in FIG. 13, simulation image 540*a* is an image in which images 541 to 545 of makeup of FIG. 11 and image 547*a* indicating application of concealer for concealing dark circle are superimposed. In addition, in information display area 546*a*, the cosmetics information of concealer and cosmetics information of cosmetics for the skin in consideration of the fact that the skin easily dries than usual are displayed.

By proposing makeup/skin care suitable for the change in face condition in this manner, it is possible to maintain the appearance of FIG. 11 which is excellent in aesthetics even when the face condition of the user is changed from the condition illustrated in FIG. 8 to the condition illustrated in FIG. 12.

It is to be noted that when only the image of the concealer is displayed during the makeup simulation, the position and density of the concealer cannot be easily visually recognized. For this reason, desirably, the application region is indicated by dotted line or the like and the application amount is displayed as text in simulation image 540*a*.

<Effect of Present Embodiment>

As described above, makeup assisting apparatus 100 according to the present embodiment presents to the user makeup/skin care selected based on physical condition information. Thus, makeup assisting apparatus 100 can perform assistance of makeup/skin maintenance more appropriately.

<Presentation of Physical Condition Level>

It is to be noted that makeup assisting apparatus 100 may present, to the user, facial change after a certain time which is estimated from the above-described physical condition level or physical condition information together with makeup/skin care. In this manner, the user can objectively determine the physical condition of the user, and can know facial change of the user in advance.

<Options of Makeup>

While makeup assisting apparatus 100 selects one type of makeup from the facial feature value and the physical condition information, the present invention is not limited to this configuration. For example, makeup assisting apparatus 100 may present a plurality of types of makeup as options and set the selected type of makeup as a target to be presented by makeup/skin care presenting section 290.

In this case, for example, makeup assisting apparatus 100 selects a plurality of types of makeup at makeup/skin care selecting section 280, and makes display section 300 display identification information of the selected plurality of types of makeup. In makeup assisting apparatus 100, makeup/skin care information of makeup selected by the user through operation on a display with touch panel, or the like from makeup/skin care selecting section 280 to makeup/skin care presenting section 290. In this case, preferably, makeup assisting apparatus 100 receives from the user an instruction to switch makeup to be presented at an arbitrary timing. Accordingly, the user can promptly judge makeup which is appropriate and which suits the user's taste from the plurality of types of makeup.

<Other Methods for Selecting Makeup>

In addition, selection of makeup/skin care based on physical condition information is not limited to the above-described examples.

For example, makeup assisting apparatus 100 may store a table in which makeup/skin care is associated with each of a plurality of types of parameters relating to physical condition information, and select makeup/skin care for each of the types of parameters. For example, makeup assisting apparatus 100 selects makeup using concealer for concealing dark circles below the eyes based only on the sleeping hours, and selects skin care using serum based only on the body temperature.

Examples of the way of selection of makeup/skin care by makeup assisting apparatus 100, which include the above-described examples, are as follows:

(1) when the body temperature is greater than a threshold, highly moisture cosmetics that prevent drying are selected;

(2) during menstruation, low irritation cosmetics are selected;

(3) when the degree of sleep or the active level estimated from sleeping hours or the like is low, concealer, a makeup color that improves appearance of ruddiness, or facial massage is selected; and (4) when the fatigue level of the eyes estimated from the opening degree of eyelids (in the vertical direction relative to the normal state) and the frequency of eyeblink are greater than a threshold, makeup that improves brightness of the eyes, or massage of the eyes is selected.

In addition, for example, makeup assisting apparatus 100 may operate in conjunction with external household electrical appliances to acquire the physical condition information through radio communication with the other external household electrical appliances. For example, makeup assisting apparatus 100 estimates change in physical condition of the user from data about food cooked with a microwave oven or the like, and selects makeup/skin care suitable for the physical condition of the user. To be more specific, for example, when lipid-rich food has been ingested, makeup assisting apparatus 100 selects makeup/skin care on the premise of increase in sebum secretion. To be more specific, for example, makeup assisting apparatus 100 selects powder foundation instead of liquid foundation, or selects relatively moisture-rich lotion instead of oil-rich milky lotion.

In addition, makeup assisting apparatus 100 may select makeup to be presented based on parameters other than the facial feature value. For example, makeup assisting apparatus 100 may preferentially select makeup which is highly appreciated by people other than the user, such as makeup which is highly appreciated by an unspecified number of users on the Internet. In addition, for example, makeup assisting apparatus 100 may select makeup based on the age or residential area of the user.

<Application of Cosmetics Information>

Further, makeup assisting apparatus 100 may associate link information to a web site where the user can purchase the skin cosmetics with the displayed cosmetics information. In this case, when the user performs operation to determine the makeup, makeup assisting apparatus 100 can display the corresponding web site through the Internet, which can assist the makeup further effectively. Further, it is possible to promote sales of cosmetics for cosmetics companies.

<Other Information to be Presented>

Further, makeup assisting apparatus 100 may create and display a simulation image of the face for which makeup has been halfway finished instead of the simulation image of the face for which all the makeup has been applied. Further, if an application order is set for each makeup as described above, makeup assisting apparatus 100 may sequentially create and display simulation images of the face for which makeup has been halfway finished according to the application order. Accordingly, makeup assisting apparatus 100 can present to the user an appropriate order of the makeup.

Further, makeup assisting apparatus 100 may present association with the area of the selected makeup and color and concentration of the selected makeup using text. This text is, for example, "apply blush of item number b55 of company B1 heavily to a range with a diameter of about 4 cm centering around the highest points of the both cheekbones," "apply concealer of item number 78 of company B2 lightly to a range of a width of 1 cm below the both eyes," or the like. Some users can imagine the face to which makeup has been applied only from the text information. It is possible to sufficiently assist such users to apply makeup even with such a presenting method.

<Other Presenting Methods>

In addition, makeup assisting apparatus 100 may present makeup/skin care using a method other than display of the simulation image.

For example, makeup assisting apparatus 100 is connected to a printer which transfers a cosmetic agent of the skin cosmetics to a predetermined thin film (a sheet-like medium). This thin film holds the transferred cosmetic agent in such a way as to be easily peeled off. Therefore, the cosmetic agent on the thin film is easily transferred to the skin by being pressed against the skin.

Makeup assisting apparatus 100 sets the same shape and area as those of an area in real space of the captured face to the thin film at makeup/skin care presenting section 290 and instructs the printer to transfer makeup to the corresponding area. It should be noted that the thin film may be either a planar shape or a steric shape.

Accordingly, makeup assisting apparatus 100 can present to the user makeup on the thin film in association with the corresponding area.

The user can actually put on the makeup selected based on the simulation image by pressing the entire thin film against the face while aligning positions indicating the corners of the both eyes printed on the thin film to the corners of the both eyes of the user. That is, the user can put on desired makeup easily and quickly without applying a cosmetic agent for each facial part.

<Variations with Other Configurations>

In addition, the above-described various types of tables may not be stored in makeup assisting apparatus 100. For example, if makeup assisting apparatus 100 can be connected to a network, makeup assisting apparatus 100 can access a server on the network in which the above-described tables are stored and can select makeup/skin care.

Further, makeup assisting apparatus 100 may be a distributed arrangement system, for example, a system in which, among functional sections illustrated in FIG. 2, only capturing section 210 and display section 300 are disposed at a terminal of the user and the other sections of the apparatus are disposed on a server on the network, or the like.

Further, physical condition acquiring section 260 may detect outside light and acquire the facial feature value in a state where the influence of external light is reduced from the image.

Further, the specific items of makeup/skin care are not limited to the above-described examples. For example, makeup to be presented includes the way of applying mascara, the way of applying lip gloss, and the like. In addition, skin care to be presented includes the way of facial massage, the way of diet and the like.

In addition, makeup assisting apparatus 100 may present skin care in conjunction with external household electrical appliances through radio communication with the external household electrical appliances.

For example, makeup assisting apparatus 100 may operate in conjunction with a refrigerator and select food that improves the physical condition or facial condition of the user from the food in the refrigerator based on the physical condition information of the user. In this case, makeup assisting apparatus 100 presents to the user a message requesting to intake the selected food.

In addition, for example, makeup assisting apparatus 100 may operate in conjunction with an air-conditioner and set an environmental condition that improves the physical condition or facial condition of the user as a target environmental condition based on the physical condition information of the user. In this case, makeup assisting apparatus 100 controls the operation of the air-conditioner to bring the indoor condition closer to the target environmental condition.

In addition, for example, makeup assisting apparatus 100 may operate in conjunction with an AV (Audio Video) apparatus and select a television program that provides information that improves the physical condition or facial condition of the user based on the physical condition information of the user. In this case, makeup assisting apparatus 100 controls a video recorder to display or record the selected television program.

In addition, for example, makeup assisting apparatus 100 may be connected to skin care equipment such as a steamer and facial equipment and present to the user equipment information such as the way of using the above-described skin care equipment at makeup/skin care presenting section 290. In this case, makeup/skin care presenting section 290 may, for example, communicate with the connected equipment and acquire the equipment information from the equipment or acquire only identification information from the equipment and acquire the corresponding equipment information from the Internet.

A makeup assisting apparatus of the present disclosure includes: a physical condition acquiring section that acquires physical condition information relating to a physical condition of a person who is subjected to makeup and/or skin maintenance; a makeup/skin care selecting section that selects make-up and/or skin care based on the acquired physical condition information, the make-up being a way of performing the makeup, the skin care being a way of performing the skin maintenance; and a makeup/skin care presenting section that presents the selected makeup and/or the selected skin care to a user who performs the makeup and/or the skin maintenance.

Preferably, the makeup assisting apparatus further includes: a makeup/skin care table storing section that stores a makeup/skin care table, the makeup/skin care table describing, in association with each of a plurality of contents of the physical condition information, the makeup and/or the skin care suitable for change in a facial condition of the person that is estimated when a physical condition of the person matches any of the contents of the physical condition information, in which the makeup/skin care selecting section refers to the makeup/skin care table and selects the makeup and/or the skin care corresponding to a content of the acquired physical condition information.

Preferably, the makeup assisting apparatus further includes: an image acquiring section that acquires a captured image of a face of the person; and a facial part acquiring section that acquires an area of a facial part of the face from the image, in which the makeup/skin care selecting section selects the make-up for each of the facial parts, and the makeup/skin care presenting section creates a simulation image obtained by superimposing, on the image, another image indicating a state of the make-up when the make-up is applied to the face, and presents the created simulation image.

Preferably, in the makeup assisting apparatus, the physical condition information relates to at least one of sleeping hours, a body temperature, an amount of physical activity, an opening degree of an eyelid, a frequency of eyeblink, a stage in a menstrual cycle, a blood pressure, and a skin condition.

Preferably, in the makeup assisting apparatus, the plurality of contents of the physical condition are a plurality of physical condition levels corresponding to quality levels of the physical condition, the makeup assisting apparatus further includes: a sensor information acquiring section that acquires, as sensor information, at least one of the sleeping hours, the body temperature, the amount of physical activity, the opening degree of an eyelid, the frequency of eyeblink, the stage in a menstrual cycle, the blood pressure, and the skin condition; and a physical condition table storing section that stores a physical condition table describing correspondence relationships among the plurality of contents of the sensor information and the plurality of physical condition levels, and the physical condition acquiring section refers to the physical condition table, and acquires the physical condition level corresponding to the acquired sensor information.

Preferably, in the makeup assisting apparatus, the change in the facial condition includes change in a degree of at least one of drying of skin, secretion of sebum, secretion of sweat, dark circle, wrinkles, slack of skin, relaxation of muscle, excitation of muscle, poorness of complexion, and rough skin.

Preferably, the makeup assisting apparatus further includes: an image capturing section that captures a moving image of the face; and a display section that displays the simulation image to the user, in which the image acquiring section acquires images included in the moving image, and the makeup/skin care presenting section sequentially creates the simulation images for the respective images included in the moving image while keeping the make-up selected once for the moving image, and makes the display section sequentially display the simulation images.

Preferably, in the makeup assisting apparatus, a facial feature value of the face to be acquired and the make-up are further associated with one another in the makeup/skin care table, the makeup/skin care selecting section acquires the facial feature value of the face, and refers to the makeup/skin care table to select the make-up corresponding to the acquired facial feature value.

A makeup assisting method of the present disclosure includes: acquiring physical condition information relating to a physical condition of a person who is subjected to makeup and/or skin maintenance; selecting make-up and/or skin care based on the acquired physical condition information, the make-up being a way of performing the makeup, the skin care being a way of performing the skin maintenance; and presenting the selected makeup and/or the selected skin care to a user who performs the makeup and/or the skin maintenance.

A makeup assisting program of the present disclosure causes a computer to execute processing including: acquiring physical condition information relating to a physical condition of a person who is subjected to makeup and/or skin maintenance; selecting make-up and/or skin care based on the acquired physical condition information, the make-up being a way of performing the makeup, the skin care being a way of performing the skin maintenance; and presenting the selected makeup and/or the selected skin care to a user who performs the makeup and/or the skin maintenance.

It is to be noted that the program may be recorded in a recording medium which can be read by a computer. The recording medium may be a recording medium such as a flash memory.

This application is entitled to and claims the benefit of Japanese Patent Application No. 2013-039138 dated Feb. 28, 2013, the disclosure of which including the specification, drawings and abstract is incorporated herein by reference in its entirety.

INDUSTRIAL APPLICABILITY

The present invention is useful as a makeup assisting apparatus, a makeup assisting method and a makeup assisting program which can appropriately assist makeup/skin maintenance.

REFERENCE SIGNS LIST

100 Makeup assisting apparatus
210 Image capturing section
220 Image acquiring section
230 Sensor information acquiring section
240 Facial part acquiring section
250 Physical condition table storing section
260 Physical condition acquiring section 270 Makeup/skin care table storing section
280 Makeup/skin care selecting section
290 Makeup/skin care presenting section
300 Display section

The invention claimed is:

1. A makeup assisting apparatus that presents makeup and/or skin care depending on a physical condition of a person subjected to makeup and/or skin maintenance, the apparatus comprising:
a display;
a camera that captures an image of a face of a person;
at least one sensor including at least one of a sleep meter, a thermometer or a physical activity meter that numerically measure sleeping hours, a body temperature and an amount of physical activity;
a processor and a memory,
wherein the memory stores a physical condition table and a makeup/skin care table,
the physical condition table describes correspondence relationships between a plurality of contents of sensor information and physical condition levels, the physical condition levels being values indicating quality levels of human physical conditions,
the makeup/skin care table describes, in association with one another:
the physical condition levels and makeup and/or skin care suitable for an estimated change in a facial condition of the person after a lapse of a predetermined period of time,
wherein the processor is configured to:
acquire the captured image of the face of the person;
communicably connect to the at least one sensor, and acquire at least one parameter as the sensor information, the at least one parameter including at least one of the sleeping hours, the body temperature, or the amount of physical activity measured by the sleep meter, the thermometer and the physical activity meter;
determine a physical condition level of the person corresponding to the acquired sensor information by referring to the physical condition table;
select makeup and/or skin care associated with the determined physical condition level of the person by referring to the makeup/skin care table; and
create a simulation image by superimposing, on the captured image, an image indicating the selected makeup and/or the selected skin care in a state where the selected makeup and/or the selected skin care are/is applied to the face, and display, on the display, the created simulation image,
wherein the makeup/skin care table stored in the memory further includes facial feature value groups, each being in association with the makeup and/or the skin care and the physical condition levels,
the processor is further configured to:
acquire a facial feature value of the face of the person by analyzing the captured image of the face of the person, the facial feature value being multivariate data including a plurality of values indicating features of the face of the person,
determine a facial feature value group of the acquired facial feature value, by determining a distance between the acquired facial feature value and a representative value of each of the facial feature value groups, and
select the makeup and/or the skin care associated with the determined facial feature value group and the determined physical condition level of the person by referring to the makeup/skin care table,
wherein, the processor
acquires images in a moving image captured by the camera, and
sequentially creates simulation images for the respective images included in the moving image while keeping the selected make-up and/or the selected skin care for the moving image, and sequentially displays, on the display, the sequentially created simulation images,
wherein the makeup assisting apparatus further comprises
a printer that transfers a cosmetic agent of skin cosmetics corresponding to the selected makeup and/or the selected skin care to an area of a thin film corresponding to the selected makeup and/or the selected skin care, such that the thin film holds the cosmetic agent to be easily peeled off and transferred to a skin of the person when the thin film is pressed against the skin of the person.

2. The makeup assisting apparatus according to claim 1 wherein the processor is further configured to:
acquire areas of facial parts of the face from the captured image;
select the make-up and/or the skin care for each of the facial parts, and
create the simulation image by superimposing, on the captured image, the image indicating the selected makeup and/or the selected skin care in a state where the selected make-up and/or the selected skin care are/is applied to the face, based upon the selected make-up and/or the skin care for each of the facial parts.

3. The makeup assisting apparatus according to claim 1, wherein the change in the facial condition includes change in a degree of at least one of dryness of skin, secretion of sebum, secretion of sweat, dark circle, wrinkles, skin slackness, muscle relaxation, muscle excitation, poorness of complexion, and rough skin.

4. The makeup assisting apparatus according to claim 1, wherein:
the physical condition table describes at least the correspondence relationships between the sleeping hours and the body temperature and the physical condition levels,
the sensor includes at least the sleep meter and the thermometer, and
the processor determines the physical condition level of the person corresponding to the sleeping hour acquired by the sleep meter and the body temperature acquired by the thermometer.

5. The makeup assisting apparatus according to claim 1, wherein
the processor superimposes the image indicating the selected makeup and/or the selected skin care on the captured image, by using an alpha blending process, which is defined by the following equations:

$$R = r_2 \times \alpha + r_1 \times (1-\alpha),$$

$$G = g_2 \times \alpha + g_1 \times (1-\alpha),$$

$$B = b_2 \times \alpha + b_1 \times (1-\alpha),$$

where $r_1$, $g_1$ and $b_1$ are the RGB values of an area in the captured image, $r_2$, $g_2$ and $b_2$ are the RGB values of the corresponding area in the image indicating the selected makeup and/or the selected skin care, R, G and B are RGB values of the corresponding area in the simulation image, and α is a value set according to concentration of the selected makeup.

6. A makeup assisting method for a makeup assisting device including a memory, a processor, a display and a printer, and is connectable to a camera and at least one sensor including at least one of a sleep meter, a thermometer or a physical activity meter that numerically measure sleeping hours, a body temperature, and an amount of physical activity, the makeup assisting method presenting makeup and/or skin care depending on a physical condition of a person subjected to makeup and/or skin maintenance, the method comprising:

acquiring an image of a face of the person captured by the camera;

communicably connecting to the at least one sensor, and acquiring at least one parameter as sensor information, the at least one parameter including at least one of the sleeping hours, the body temperature, or the amount of physical activity measured by the sleep meter, the thermometer and the physical activity meter;

determining a physical condition level of the person corresponding to the acquired sensor information, by referring to a physical condition table, the physical condition table being stored in a memory and describing correspondence relationships between a plurality of contents of sensor information and physical condition levels, the physical condition levels being values indicating quality levels of human physical conditions;

selecting makeup and/or skin care associated with the determined physical condition level of the person, by referring to a makeup/skin care table, the makeup/skin care table being stored in the memory and describing, in association with one another:

the physical condition levels and makeup and/or skin care suitable for an estimated change in a facial condition of the person after a lapse of a predetermined period of time; and creating a simulation image by superimposing, on the captured image, an image indicating the selected makeup and/or the selected skin care in a state where the selected makeup and/or the selected skin care are/is applied to the face, and displaying, on the display, the created simulation image, wherein the makeup/skin care table stored in the memory further includes facial feature value groups, each being in association with the makeup and/or the skin care and the physical condition levels, the method further comprising:

acquiring a facial feature value of the face of the person by analyzing the captured image of the face of the person, the facial feature value being multivariate data including a plurality of values indicating features of the face of the person, determining a facial feature value group of the acquired facial feature value, by determining a distance between the acquired facial feature value and a representative value of each of the facial feature value groups, and selecting the makeup and/or the skin care associated with the determined facial feature value group and the determined physical condition level of the person by referring to the makeup/skin care table, wherein, the method further comprises:

acquiring images in a moving image captured by the camera, and sequentially creating simulation images for the respective images included in the moving image while keeping the selected make-up and/or the selected skin care for the moving image, and sequentially displaying, on the display, the sequentially created simulation images, wherein the method further comprises:

causing the printer to transfer a cosmetic agent of skin cosmetics corresponding to the selected makeup and/or the selected skin care to an area of a thin film corresponding to the selected makeup and/or the selected skin care, such that the thin film holds the cosmetic agent to be easily peeled off and transferred to a skin of the person when the thin film is pressed against the skin of the person.

7. A non-transitory computer readable medium that stores a makeup assisting program that presents makeup and/or skin care depending on a physical condition of a person subjected to makeup and/or skin maintenance, the program causing a computer to execute processing comprising:

acquiring an image of a face of the person captured by a camera;

communicably connecting to at least one sensor including at least one of a sleep meter, a thermometer or a physical activity meter that numerically measure sleeping hours, a body temperature, and an amount of physical activity, and acquiring, from at least one sensor, at least one parameter as sensor information, the at least one parameter including the at least one of the sleeping hours, the body temperature, or the amount of physical activity measured by the sleep meter, the thermometer and the physical activity meter;

determining a physical condition level of the person corresponding to the acquired sensor information, by referring to a physical condition table, the physical condition table being stored in a memory and describing correspondence relationships between a plurality of contents of sensor information and physical condition levels, the physical condition levels being values indicating quality levels of human physical conditions;

selecting makeup and/or skin care associated with the determined physical condition level of the person, by referring to a makeup/skin care table, the makeup/skin care table being stored in the memory and describing, in association with one another:

the physical condition levels and makeup and/or skin care suitable for an estimated change in a facial condition of the person after a lapse of a predetermined period of time; and creating a simulation image by superimposing, on the captured image, an image indicating the selected makeup and/or the selected skin care in a state where the selected makeup and/or the selected skin care are/is applied to the face, and displaying, on a display, to the created simulation image, wherein the makeup/skin care table stored in the memory further includes facial feature value groups, each being in association with the makeup and/or the skin care and the physical condition levels, the program further causing the computer to execute processing comprising:

acquiring a facial feature value of the face of the person by analyzing the captured image of the face of the person, the facial feature value is multivariate data including a plurality of values indicating features of the face of the person, determining a facial feature value group of the acquired facial feature value, by determining a distance between the acquired facial feature value and a representative value of each of the facial feature value groups, and selecting the makeup and/or the skin care associated with the determined facial feature value group and the determined physical condition level of the person by referring to the makeup/skin care table, the program further causing the computer to execute processing comprising:

acquiring images in a moving image captured by the camera, and sequentially creating simulation images for the respective images included in the moving image while keeping the selected make-up and/or the selected skin care for the moving image, and sequentially displaying, on the display, the sequentially created simulation images, the program further causing the computer to execute processing comprising:

causing a printer to transfer a cosmetic agent of skin cosmetics corresponding to the selected makeup and/or the selected skin care to an area of a thin film corresponding to the selected makeup and/or the selected skin care, such that the thin film holds the cosmetic agent to be easily peeled off and transferred to a skin of the person when the thin film is pressed against the skin of the person.

\* \* \* \* \*